United States Patent [19]
Wright

[11] Patent Number: 6,034,073
[45] Date of Patent: *Mar. 7, 2000

[54] SOLVENT DETERGENT EMULSIONS HAVING ANTIVIRAL ACTIVITY

[75] Inventor: D. Craig Wright, Gaithersburg, Md.

[73] Assignee: Novavax, Inc., Columbia, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/593,651

[22] Filed: Jan. 29, 1996

Related U.S. Application Data

[63] Continuation-in-part of application No. 08/427,042, Apr. 24, 1995, abandoned.

[51] Int. Cl.[7] .......................... A01N 57/26; A01N 43/16; A01N 43/08
[52] U.S. Cl. ........................ 514/77; 514/460; 514/470; 514/473
[58] Field of Search ........................ 514/77, 460, 470, 514/473

[56] References Cited

U.S. PATENT DOCUMENTS

| | | | |
|---|---|---|---|
| 4,020,183 | 4/1977 | Asculai et al. | 424/341 |
| 4,540,573 | 9/1985 | Neurath et al. | 424/85 |
| 4,909,940 | 3/1990 | Horowitz et al. | 210/634 |
| 5,186,945 | 2/1993 | Shanbrom | 424/529 |

OTHER PUBLICATIONS

M. Windholtz et al. (1983) "The Merck Index" published by Merck & Co. (Rahway, NJ), p. 1249, abstract No. 8574.

A.R. Gennaro et al. (1985) "Remington's Pharmaceutical Sciences" published by Philadelphia College of Pharmacy and Science, (Philadelphia, PA) pp. 1295, 1301–1302.

International Search Report, issued Jul. 15, 1996, application number PCT/US96/CPPC.

Henry F. Smyth, Jr., and Charles P. Carpenter, "The Place of the Range Finding Test in the Industrial Toxicology Laboratory", *Journal of Industrial Hygiene and Toxicology*, vol. 26, No. 8, pp. 269–273 (1944).

*Primary Examiner*—Russell Travers
*Attorney, Agent, or Firm*—Lahive & Cockfield, LLP

[57] ABSTRACT

Methods and pharmaceutical compositions for inactivating an envelope virus using an oil-in-water emulsion including an oil, a surfactant, and an organic phosphate-based solvent are disclosed. These methods can be used to inactivate a wide variety of envelope viruses, such as HIV.

29 Claims, 1 Drawing Sheet

CLINICAL DATA FROM THE ACUTE ORAL RAT TOXICITY STUDY ON BCT-100 0.1 EMULSION

| Group Designation | Group # | Rat Number | Sex | Dose Volume | Body Weight (g) Day 0 | Body Weight (g) Day 7 | Weight Gain (g) Day 7 | Body Weight (g) Day 14 | Weight Gain (g) Day 14 | Total Weight Gain (g) Days 0-14 |
|---|---|---|---|---|---|---|---|---|---|---|
| BCT-100 0.1 | 1 | 51348 | M | 3 | 187 | 264 | 77 | 316 | 52 | 129 |
| BCT-100 0.1 | 1 | 51349 | M | 3 | 204 | 288 | 84 | 352 | 64 | 148 |
| BCT-100 0.1 | 1 | 51350 | M | 3 | 199 | 301 | 102 | 361 | 60 | 162 |
| BCT-100 0.1 | 1 | 51351 | M | 3 | 203 | 290 | 87 | 345 | 55 | 142 |
| BCT-100 0.1 | 1 | 51352 | M | 3 | 186 | 269 | 83 | 314 | 45 | 128 |
| | | | | Mean wt. | 195.8 | 282.4 | 86.6 | 337.6 | 55.2 | 141.8 |
| BCT-100 0.1 | 1 | 51374 | F | 3 | 209 | 261 | 52 | 281 | 20 | 72 |
| BCT-100 0.1 | 1 | 51375 | F | 3 | 215 | 253 | 38 | 278 | 25 | 63 |
| BCT-100 0.1 | 1 | 51376 | F | 3 | 223 | 267 | 44 | 290 | 23 | 67 |
| BCT-100 0.1 | 1 | 51377 | F | 3 | 202 | 236 | 34 | 253 | 17 | 51 |
| BCT-100 0.1 | 1 | 51378 | F | 3 | 218 | 254 | 36 | 267 | 13 | 49 |
| | | | | Mean wt. | 213.4 | 254.2 | 40.8 | 273.8 | 19.6 | 60.4 |

FIG. 1

SOLVENT DETERGENT EMULSIONS HAVING ANTIVIRAL ACTIVITY

RELATED APPLICATIONS

This application is a continuation-in-part of application Ser. No. 08/427,042, filed Apr. 24, 1995, the contents of which are incorporated herein by reference.

BACKGROUND OF THE INVENTION

The present invention relates to a virus-inactivating oil-in-water emulsion which begins inactivating viruses upon contact.

It is known that if a water-immiscible liquid phase is mixed into an aqueous phase by mechanical agitation, for example, by means of an ultra-disperser, a dispersion, such as an oil-in-water emulsion, will develop. The stability of the resulting dispersion may require the addition of an emulsifying agent, the molecules of which are adsorbed onto the oil/water interface to form a kind of continuous membrane which prevents direct contact between two adjacent droplets. One advantage of oil-in-water emulsions is that they may readily be diluted with water to a desired composition.

In addition to discrete oil droplets dispersed in an aqueous phase oil-in-water emulsions can also contain other lipid structures, such as small lipid vesicles (i.e., lipid spheres which often consist of several substantially concentric lipid bilayers separated from each other by layers of aqueous phase), micelles (i.e., amphiphile molecules in small clusters of 50–200 molecules arranged so that the polar head groups face outward toward the aqueous phase and the a polar tails are sequestered inward away from the aqueous phase), or lamellar phases (lipid dispersions in which each particle consists of parallel amphiphile bilayers separated by thin films of water). These lipid structures are formed as a result of hydrophobic forces which drive apolar residues (i.e.,long hydrocarbon chains) away from water.

The portals of entry of pathogenic bacteria, viruses or fungi are predominantly the skin and mucus membranes, including the upper and lower respiratory tracts. The first step in many infections is attachment or colonization on skin or mucus membranes, followed by subsequent invasion and dissemination of the infectious pathogen. Accordingly, it is desirable to provide a virus-inactivating formulation which inactivates viruses on contact.

Detergents and solvents have been used to inactivate viruses in blood or plasma derived products, as described in U.S. Pat. No. 4,540,573 to Neurath, the contents of which are hereby incorporated by reference. This patent teaches the use of aqueous solutions of trialkylphosphates to inactivate viruses in blood-derived products in vitro. However, after treatment of the blood-derived product according to this method, the trialkyl phosphate must then be removed by methods such as dialysis or lyophilization, necessitating additional extraction steps (as described in U.S. Pat. No. 4,909,940 to Horowitz, the contents of which are hereby incorporated by reference). This lengthy and complex procedure is not suitable for use in treating viral infections in an affected subject, nor does the patent teach or suggest in vivo uses of the solutions.

Furthermore, many trialkyl phosphates are known to be toxic or irritating to mucous membranes (see, e.g., Smyth and Carpenter (1944) *J Ind Hyg. Toxicol.* 26: 269). For these reasons, they have not been thought to be usable in preparations intended for in vivo administration.

Accordingly, an object of the present invention is to provide a virus-inactivating emulsion which inactivates viruses on contact. It is a further object of the invention to provide a non-irritating, stable preparation that inactivates viruses, especially envelope viruses, on the skin or mucous membranes.

Another object of the present invention is to provide a method of inactivating a virus by contacting the virus with a virus-inactivating emulsion.

Another object of the present invention is to provide a method of preventing a viral infection in an affected subject by administering a virus-inactivating emulsion to the subject.

SUMMARY OF THE INVENTION

The present invention provides a stable oil-in-water emulsion for inactivating viruses upon contact. The emulsion of the present invention consists primarily of droplets of an oily discontinuous phase dispersed in an aqueous continuous phase, such as water. The discontinuous phase is prepared from a surfactant, an oil carrier, and an organic phosphate-based solvent such as tri-n-butyl phosphate. The emulsions of the present invention are highly stable, and are not decomposed even after long storage periods.

Virus-inactivating emulsions of the present invention are non-toxic and safe when swallowed, inhaled, or applied to the skin. This is in contrast to trialkyl phosphates themselves or standard solutions of trialkyl phosphates, which may be irritating to skin or mucous membranes.

Oils useful in forming oil-in-water emulsions of the present invention include a broad spectrum of water-immiscible materials, such as soybean oil, avocado oil, squalene oil, squalane oil, sesame oil, olive oil, canola oil, corn oil, rapeseed oil, safflower oil, sunflower oil, fish oils, flavor oils, water insoluble vitamins, and mixtures thereof.

Surfactants useful in forming emulsions of the present invention include a variety of anionic and nonionic surfactants, as well as other emulsifiers capable of promoting the formation of oil-in-water emulsions. In general, the emulsifier will be relatively hydrophilic, and blends of emulsifiers can be used to achieve the necessary qualities. Nonionic surfactants have advantages over ionic emulsifiers: they are compatible with a broad pH range and often form more stable emulsions than do ionic (e.g. soap-type) emulsifiers. Particularly useful surfactants include the detergents sold under the trademarks Tween 20, Tween 80, and Triton X-100. A most preferred surfactant is Triton X- 100 (t-octylphenoxypolyethoxyethanol).

Organic phosphate-based solvents useful in forming oil-in-water emulsions of the present invention include dialkyl and trialkyl phosphates. In a preferred embodiment, each alkyl group of the di- or trialkyl phosphate has one to ten carbon atoms, more preferably two to eight carbon atoms. The alkyl groups of the di- or trialkyl phosphate can all be the same or can be different. A particularly preferred trialkyl phosphate is tri-n-butyl phosphate, which is a plasticizer. Mixtures of different dialkyl and trialkyl phosphates can be employed.

In another embodiment of the invention, at least a portion of the emulsion may be in the form of lipid structures including, but not limited to, unilamellar, multilamellar, and paucilamellar lipid vesicles, micelles, and lamellar phases.

In another aspect, the invention features a method of inactivating a virus, where the method includes the step of providing a virus inactivating emulsion and the step of contacting the virus with the emulsion. This emulsion includes a surfactant, an organic phosphate based solvent, and a carrier oil. In preferred embodiments, the virus is an envelope virus. In certain preferred embodiments, the virus is selected from the group consisting of Herpesviridae, Togaviridae, Flaviviridae, Coronaviridae, Rhabdoviridae, Filoviridae, Paramyxoviridae, Orthomyxoviridae, Arenaviridae, Retroviridae, and Hepadnavirida. In a particularly preferred embodiment, the virus is HIV.

The present invention also provides a virus-inactivating preparation suitable for pharmaceutical administration, which may also include a pharmaceutically acceptable carrier. The preparation can be applied topically to skin surface areas, mucus membranes, or oral surfaces, for example, as a cream, gel, spray, or mouthwash, to treat or prevent viral infections. Accordingly, the present invention further provides a method for inactivating a virus by topical administration of the emulsions of the invention.

In a further embodiment, the invention includes a method of preventing viral infection in a subject by applying the emulsion of the present invention to the skin or mucous membrane of that subject to inactivate the virus. By inactivating the virus before attachment or colonization on skin or mucus membranes, subsequent invasion and dissemination of the infectious pathogen is prevented.

The invention also features virus-inactivating emulsions in preparations suitable for veterinary administration. The virus-inactivating emulsions may be used to prevent or treat such conditions as avian and swine influenza.

BRIEF DESCRIPTION OF THE DRAWING

FIG. 1 is a table showing the results of feeding an emulsion of the invention to rats.

DETAILED DESCRIPTION OF THE INVENTION

The present invention relates to virus-inactivating oil-in-water emulsions made up of droplets of an oily discontinuous phase containing an organic phosphate-based solvent dispersed in an aqueous continuous phase. The emulsion further includes a surfactant. The emulsions are stable, non-toxic, and simple and inexpensive to formulate.

The term "virus-inactivating," as used herein, means having the ability to prevent or inhibit viral infection and replication. Virus inactivation generally occurs by killing the virus. The emulsions of the present invention inactivate a wide variety of viruses, particularly envelope viruses. It appears that inactivation is achieved by adhesion or binding of one or more components of the oil phase to the viral envelope, thereby disrupting the envelope structure. Accordingly, one aspect of the present invention provides a virus-inactivating oil-in-water emulsion which contains materials capable of binding to the membrane of a virus and disrupting the membrane structure so that the virus is inactivated.

As is described in more detail in Example 2, infra, the emulsions of the present invention can inactivate viruses rapidly. In preferred embodiments, the inactivation of viruses occurs after no more than six hours, more preferably after no more than two hours, and even more preferably in less than one hour after the virus is contacted with an emulsion according to the present invention.

The term "emulsion," as used herein, includes classic oil-in-water dispersions or droplets, as well as other lipid structures which can form as a result of hydrophobic forces which drive a polar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases.

Virus-inactivating oil-in-water emulsions of the present invention can be formed using classic emulsion forming techniques known in the art. In brief, the oily phase is mixed with the aqueous phase under relatively high shear forces to obtain an oil-in-water emulsion containing oil droplets which are approximately 1 micron in diameter. The oily discontinuous phase is formed by blending (a) an oil carrier; (b) a surfactant; and (c) an organic phosphate-based solvent.

Once the oily phase is formed, it is heated and blended with an aqueous phase (e.g., water, saline, or any other aqueous solution which can hydrate the lipids) on a volume-to-volume basis ranging from about 1: 5 to 1: 1, preferably about 1: 4 oily phase to aqueous phase The oil and aqueous phases can be blended using any apparatus capable of producing shear forces sufficient to form an emulsion, including, for example, French Press, Novamix™ (IGI Inc., Buena N.J.) or syringe mixer, or by hand, using two syringes.

Virus-inactivating oil-in-water emulsions of the present invention can be used to inactivate a variety of viruses upon contact. For example, the presently disclosed emulsions can be used for oropharyngeal, oral, venereal, or rectal application to inactivate, or prevent infection secondary to, viruses including Herpesviridae (e.g., herpes simplex types 1 and 2, Epstein-Barr virus, cytomegalovirus, varicella virus, and human herpes virus type 6), Togaviridae (e.g., Rubella virus), Flaviviridae, (e.g., Yellow Fever virus), Coronaviridae (e.g., Corona viruses), Rhabdoviridae (e.g., Rabies virus), Filoviridae (e.g., Marburg virus), Paramyxoviridae (e.g., Measles virus), Orthomyxoviridae (e.g., Influenza viruses), Arenaviridae (e.g., Lymphocytic choriomeningitis virus), Retroviridae (e.g., HIV-1), and Hepadnavirida (e.g., Hepatitis B). In a preferred embodiment of the invention, the oil-in-water emulsions are used to inactivate HIV.

The present invention also provides a virus-inactivating preparation suitable for pharmaceutical administration consisting of an oil-in-water emulsion of the present invention and a pharmaceutically acceptable carrier. The term "pharmaceutically acceptable carrier," as used herein, refers to any physiologically compatible carrier for stabilizing emulsions of the present invention for pharmaceutical administration. Use of such media and agents for pharmaceutically active substances is well known in the art. Except insofar as any conventional media or agent is incompatible with the emulsions of the present invention, use thereof in a pharmaceutical preparation is contemplated.

The present invention further provides methods for inactivating viruses by topical administration of an oil-in-water emulsion of the present invention, preferably in the form of a pharmaceutical preparation. The term "topical," as used herein, includes application to mucous membranes, oral surfaces, skin, and the surfaces of any bodily orifice, such as the vagina or rectum.

The following examples will illustrate the efficacy of the invention.

EXAMPLES

Example 1

In this Example, several virus-inactivating oil-in-water emulsions, each including a surfactant and a trialkyl phosphate, were formed and characterized.

The emulsions were formed as follows: an oil phase was made by blending tributyl phosphate, soybean oil, and a surfactant (either Triton X- 100, Tween 20 or Tween 80) and then heating the resulting mixture at 86° C. for one hour. An emulsion was then produced by injecting water into the oil phase at a volume/volume ratio of one part oil phase to four parts water. The emulsions were produced manually, with reciprocating syringe instrumentation, or with continuous flow instrumentation. Table 1 shows the proportions of each component, the pH, and the size of the oily droplets of the emulsions as measured on a Coulter LS 130 laser sizing instrument equipped with a circulating water bath.

TABLE 1

| Chemical Components of Emulsion | Percentage of Each Component | pH | Mean Coulter Size in Microns | Mean Coulter Range in Microns |
| --- | --- | --- | --- | --- |
| Triton X-100 | 2% | 5.16 | 1.074 | 0.758–1.428 |
| Tributylphosphate | 2% | | | |
| Soybean oil | 16% | | | |
| Water for injection (BCT-100) | 80% | | | |
| Triton X-100 | 0.20% | 5.37 | 0.944 | 0.625–1.333 |
| Tributyl phosphate | 0.20% | | | |
| Soybean oil | 1.60% | | | |
| Water for injection (BCT-100 0.1)† | 98% | | | |
| Tween 20 | 2% | 4.14 | 1.024 | 0.679–1.409 |
| Tributyl phosphate | 2% | | | |
| Soybean oil | 16% | | | |
| Water for injection | 80% | | | |
| Tween 80 | 2% | 6.04 | 1.030 | 0.706–1.380 |
| Tributyl phosphate | 2% | | | |
| Soybean oil | 16% | | | |
| Water for injection | 80% | | | |

†The BCT-100 0.1 emulsion was obtained by diluting the BCT-100 emulsion with water in a ratio of 1:9.

The emulsions of the present invention are highly stable. The BCT-100 and BCT-100 0.1 emulsions have been found to be substantially unchanged after storage at room temperature for at least seven months.

Example 2

In this Example, the BCT- 100 and BCT-100 0.1 emulsions produced in Example 1 were tested for viricidal and activity. The BCT-100 emulsion of the present invention is highly effective for inactivating viruses, The BCT-100 0.1 emulsion was also found to be highly effective for inactivating viruses.

Viricidal Assay 100 microliters of HIV-1$_{Mn}$ 1000×pelleted virus Lot #50-013 (TCID-50/ml=$10^{-6}$) was mixed for 30 minutes with either 100 microliters of water for injection or 100 microliters of the BCT-100 emulsion. 1.8 ml of tissue culture medium was then added to each preparation. Serial ten-fold dilutions of BCT- 100 were made and 0.4 ml of each $10^{-2}$ to $10^{-6}$ dilution was placed in tubes containing C8166 cells, a HTLV-1 transformed T cell line. These combined materials were then incubated at 37° C. for either two or six hours, washed three times in phosphate buffered saline (PBS), resuspended in fresh medium, and each dilution plated in four replicate wells. Cells were fed twice weekly. Cells were observed at seven and fourteen days for cytopathic effects, and supernatants were collected for p24 assay determinations as confirmation of viral proliferation (immunoassay with calorimetric measurement). Tissue culture infectious dose (TCID-50) calculations were performed based on the results of the p24 determinations.

The result of the viricidal assay for two hour incubation is shown in Table 2.

TABLE 2

| Test Article | TCID-50 after 7 day Incubation | TCID-50 after 14 day Incubation |
| --- | --- | --- |
| Water | $10^{-3.5}$ | $10^{-5.25}$ |
| BCT-100 Emulsion | 0 | $10^{-0.25}$ |

The results shown in Table 2 demonstrate that the emulsion-treated sample had a 3.5 log virus reduction in TCID-50 at seven days compared to the water control, and a five log virus reduction in TCID-50 at fourteen days, after a two hour incubation.

The results of the viricidal assay for six hour incubation is shown in Table 3:

TABLE 3

| Test Article | TCID-50 after 7 day Incubation | TCID-50 after 14 day Incubation |
| --- | --- | --- |
| Water | $10^{-3.25}$ | $10^{-4}$ |
| BCT-100 Emulsion | 0 | 0 |

The results shown in Table 3 demonstrate that the emulsion-treated sample had a 3.25 log virus reduction in TCID-50 at seven days compared to the control, and a four log virus reduction in TCID-50 at fourteen days after a six hour incubation.

Assays of the viricidal activity of the BCT-100 0.1 emulsion were performed as above for the BCT-100 emulsion, at both two hour and six hour incubations. The results are shown in Tables 4 and 5.

TABLE 4

| Test Article | TCID-50 after 7 day Incubation | TCID-50 after 14 day Incubation |
| --- | --- | --- |
| Water | $10^{-4.75}$ | $10^{-4.75}$ |
| BCT-100 0.1 Emulsion | 0 | 0 |

The results shown in Table 4 demonstrate that the emulsion-treated sample had a 4.75 log virus reduction in TCID-50 at seven and fourteen days, compared to the control sample, after a two hour incubation.

The result of the viricidal assay for six hour incubation is shown in Table 5:

TABLE 5

| Test Article | TCID-50 after 7 day Incubation | TCID-50 after 14 day Incubation |
| --- | --- | --- |
| Water | $10^{-4.5}$ | $10^{-5.25}$ |
| BCT-100 0.1 Emulsion | 0 | 0 |

The results shown in Table 5 demonstrate that the emulsion-treated sample had a 4.5 log virus reduction in TCID-50 at seven days, and a 5.25 log virus reduction in TCID-50 at fourteen days, after a six hour incubation.

The BCT-100 0.1 emulsion was also tested against several other viruses, both envelope viruses such as HSV, and non-envelope viruses, such as adenovirus. In general, the assays were performed according to the above procedure, using host cells appropriate for each virus. Cells were incubated with virus, in the presence or absence of BCT-100

0.1 emulsion, for two hours, as described above. The viruses tested and host cells used, are shown in Table 6.

TABLE 6

| Virus | Host Cell |
|---|---|
| Herpes Simplex Virus 1 (HSV-1) | VERO |
| Herpes Simplex Virus 2 (HSV-2) | VERO |
| Cytomegalovirus (CMV) | HFS (human foreskin diploid fibroblasts) |
| Varicella Zoster Virus (VSV) | HFS |
| Adenovirus 5 | 293 (transformed primary embryonal kidney) |

The cell cultures were assayed for cytopathic effect at seven and fourteen days. The assay was performed by a colorimetric method (CellTiter96™ AQueous Non-Radioactive Cell Proliferation Assay, Promega Co., Madison, Wis.). The log virus reductions in TCID-50 for the BCT- 100 0.1 emulsion (compared to a distilled water control) are shown in Table 7.

TABLE 7

| Virus | Reduction in TCID-50 after 14 day Incubation |
|---|---|
| HSV-1 | $10^5$ |
| HSV-2 | $10^{5.5}$ |
| CMV | $10^6$ |
| VSV | $10^{6.75}$ |
| Adenovirus 5 | 0 |

The results shown above demonstrate that the BCT-100 emulsion and the BCT-100 0.1 emulsion are both highly effective at inactivating a variety of envelope viruses, even at the very high virus titers used in these experiments. In contrast, the BCT-100 0.1 emulsion was not effective at inactivating adenovirus, a non-envelope virus. The two emulsions show approximately equal activity under the test conditions, despite the 10-fold difference in concentration of trialkyl phosphate.

Example 3

Tributyl phosphate alone is known to be toxic and irritating to mucous membranes. However, when incorporated into the emulsions of the present invention, these characteristics are not in evidence. As described below and shown in FIG. 1, the emulsions are surprisingly non-toxic in animals.

The BCT-100 0.1 emulsion was tested for toxicity when orally administered to rats. The emulsion was administered to Sprague-Dawley rats as a three milliliter dose by gavage on day 0. The rats were weighed on days 0, 7 and 14. As can be seen from FIG. 1, all test animals survive and gain weight after administration of the viricidal emulsion. Therefore, it is apparent that the emulsion has no measurable oral toxicity, and actually appears beneficial to the animals.

The BCT- 100 0.1 emulsion was also tested for dermal toxicity in rabbits according to the protocols provided in 16 CFR §1500.3 (data not shown). The BCT-100 0.1 emulsion was not irritating to skin in the animals tested.

The contents of all references cited throughout this application are hereby incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inactivating an envelope virus comprising the steps of
   providing a storage stable, virus inactivating, oil-in-water emulsion composed of droplets having a mean particle size in the range of about 0.5 to 1.5 microns in the form of a discontinuous oil phase distributed in an aqueous phase with a non-ionic stabilizer selected from the group consisting of Tween 20, Tween 80 and Triton X-100, said nonionic stabilizer being present in between about 0.2–2% of said composition, said aqueous phase being in the form of a pharmaceutically acceptable vehicle and forming about 80–98% of said composition, said oil phase containing a carrier oil and tributyl phosphate, said tributyl phosphate forming about 0.2–2% of said composition; and
   contacting said virus with said emulsion such that said virus is inactivated.

2. The method of claim 1 wherein said surfactant is Triton X-100.

3. The method of claim 1 wherein said carrier oil is selected from the group consisting of soybean oil, avocado oil, squalane oil, squalene oil, olive oil, canola oil, corn oil, rapeseed oil, safflower oil, sunflower oil, fish oils, flavor oils, water insoluble vitamins and mixtures thereof.

4. The method of claim 3 wherein said carrier oil comprises soybean oil.

5. The method of claim 1, wherein said envelope virus is selected from the group consisting of Herpesviridae, Togaviridae, Flaviviridae, Coronaviridae, Rhabdoviridae, Filoviridae, Paramyxoviridae, Orthomyxoviridae, Arenaviridae, Retroviridae, and Hepadnavirida.

6. The method of claim 1, wherein the virus is HIV.

7. The method of claim 1, wherein the virus is selected from the group consisting of HSV-1, HSV-2, CMV and VSV.

8. A pharmaceutical composition for inactivating a virus, said composition comprising in a storage stable, virus inactivating, oil-in-water emulsion composed of droplets having a mean particle size in the range of about 0.5 to 1.5 microns in the form of an oil phase distributed in an aqueous phase with a nonionic stabilizer selected from the group consisting of Tween 20, Tween 80 and Triton X-100, said nonionic stabilizer being present in between about 0.2–2% of said composition, said aqueous phase being in the form of a pharmaceutically acceptable vehicle and forming about 80–98% of said composition, said oil phase containing a carrier oil and tributyl phosphate, said tributyl phosphate forming about 0.2–2% of said composition.

9. The pharmaceutical composition of claim 12 wherein said non-ionic stabilizer comprises Triton X-100.

10. The composition of claim 9 wherein said surfactant is Triton X-100.

11. The composition of claim 8 wherein said carrier oil consists essentially of a vegetable oil.

12. The composition of claim 11 wherein said vegetable oil comprises soybean oil.

13. A method of inhibiting viral infection caused by an envelope virus in a subject, said method comprising the steps of
   providing a storage stable, virus inactivating, oil-in-water emulsion composed of droplets having a mean particle size in the range of about 0.5 to 1.5 microns in the form of an oil phase distributed in an aqueous phase with a non-ionic selected from the group consisting of Tween 20, Tween 80 and Triton X-100, said nonionic stabilizer being present in between about 0.2–2% of said composition, said aqueous phase being in the form of a pharmaceutically acceptable vehicle and forming about 80–98% of said composition, said oil phase containing a carrier oil and tributyl phosphate, said tributyl phosphate forming about 0.2–2% of said composition; and administering said emulsion to said subject such that said emulsion contacts said envelope virus, such that viral infection is inhibited.

14. The method of claim 13 wherein said administration step further comprises administering said emulsion topically.

15. The method of claim 13 wherein said administration step further comprises administering said emulsion by means of a porous pad.

16. The method of claim 13 wherein said organic phosphate-based solvent comprises a trialkyl phosphate.

17. The method of claim 13 wherein said carrier oil consists essentially of a vegetable oil.

18. The method of claim 17 wherein said vegetable oil is soybean oil.

19. The method of claim 13, wherein the virus is selected from the group consisting of Herpesviridae, Togaviridae, Flaviviridae, Coronaviridae, Rhabdoviridae, Filoviridae, Paramyxoviridae, Orthomyxoviridae, Arenaviridae, Retroviridae, and Hepadnavirida.

20. The method of claim 13, wherein the virus is HIV.

21. The method of claim 13, wherein the virus is selected from the group consisting of HSV-1, HSV-2, CMV and VSV.

22. The method of claim 13, wherein said virus inactivating emulsion is non-toxic to the affected subject.

23. The method of claim 13, wherein said virus inactivating emulsion is not irritating to the affected subject.

24. The composition of claim 8, wherein each alkyl group of said solvent has one to ten carbon atoms.

25. The method of claim 13, wherein said emulsion is administered to said subject oropharyngeally, orally, venereally, or rectally.

26. A non-toxic composition for inactivating an envelope virus on the surface of a substrate, said composition comprising a storage stable, virus inactivating, oil-in-water emulsion composed of droplets having a mean particle size in the range of about 0.5 to 1.5 microns in the form of an oil phase distributed in an aqueous phase with a non-ionic stabilizer selected from the group consisting of Tween 20, Tween 80 and Triton X-100, said nonionic stabilizer being present in between about 0.2–2% of said composition, said oil phase containing a carrier oil and tributyl phosphate, said tributyl phosphate forming about 0.2–2% of said composition.

27. A method of inactivating an envelope virus on the surface of a substrate comprising the steps of:

providing a non-toxic composition comprising a storage stable, virus inactivating, oil-in-water emulsion composed of droplets having a mean particle size in the range of about 0.5 to 1.5 microns in the form of an oil phase distributed in an aqueous phase with a non-ionic stabilizer selected from the group consisting of Tween 20, Tween 80 and Triton X-100, said nonionic stabilizer being present in between about 0.2–2% of said composition, said oil phase containing a carrier oil and and tributyl phosphate, said tributyl phosphate forming about 0.2–2% of said composition; and contacting said envelope virus with said emulsion such that said virus is inactivated.

28. The method of claim 27, wherein said substrate is in contact with a human or animal subject.

29. The method of claim 27, wherein said substrate is the skin of a human or animal subject.

* * * * *